(12) United States Patent
Falkenberg et al.

(10) Patent No.: US 8,853,262 B2
(45) Date of Patent: Oct. 7, 2014

(54) PKA BUFFERED VITAMIN C COMPOSITION AND METHOD

(75) Inventors: Ricky L. Falkenberg, Turlock, CA (US); Harold L. Archibald, Fairfield, CA (US)

(73) Assignee: Scientific Food Solutions, LLC, Fairfield, CA (US)

(*) Notice: Subject to any disclaimer, the term of this patent is extended or adjusted under 35 U.S.C. 154(b) by 2034 days.

(21) Appl. No.: 11/675,062

(22) Filed: Feb. 14, 2007

(65) Prior Publication Data

US 2008/0193556 A1    Aug. 14, 2008

(51) Int. Cl.
| | |
|---|---|
| *A61K 31/341* | (2006.01) |
| *A61K 31/375* | (2006.01) |
| *A61K 9/16* | (2006.01) |
| *A61K 33/10* | (2006.01) |
| *A61K 33/42* | (2006.01) |
| *A61K 9/14* | (2006.01) |
| *A61K 33/08* | (2006.01) |

(52) U.S. Cl.
CPC ............. *A61K 9/143* (2013.01); *A61K 31/375* (2013.01); *A61K 9/1611* (2013.01); *A61K 33/10* (2013.01); *A61K 33/42* (2013.01); *A61K 33/08* (2013.01)
USPC .......................... 514/461; 514/183

(58) Field of Classification Search
CPC ................................... A61K 31/341
USPC ......................................... 514/461
See application file for complete search history.

(56) References Cited

U.S. PATENT DOCUMENTS

| | | | | | |
|---|---|---|---|---|---|
| 2,836,540 | A | * | 5/1958 | Hardt | 424/683 |
| 5,624,906 | A | * | 4/1997 | Vermeer | 514/23 |
| 5,780,451 | A | * | 7/1998 | DeMichele et al. | 514/54 |
| 6,352,713 | B1 | * | 3/2002 | Kirschner et al. | 424/441 |
| 6,451,341 | B1 | * | 9/2002 | Slaga et al. | 424/468 |
| 2006/0217385 | A1 | * | 9/2006 | Edwards et al. | 514/251 |
| 2007/0248542 | A1 | * | 10/2007 | Kane et al. | 424/9.1 |

* cited by examiner

*Primary Examiner* — Jeffrey Lundgren
*Assistant Examiner* — Meghan Finn
(74) *Attorney, Agent, or Firm* — Brennan C. Swain, Esq.; Jeffer Mangels Butler & Mitchell LLP (57) ABSTRACT

A pKa buffered vitamin C composition which includes a base alkalizer composition mixed with vitamin C (calcium ascorbate or ascorbic acid). The base alkalizer composition can be approximately 24% to 40% and the ascorbic acid or calcium ascorbate can be approximately 76% to 60% by weight of the vitamin C composition. When this vitamin C composition is orally administered to an individual (in capsule or tablet form), a rapid neutralization of his stomach acid occurs followed by a sustained pH of 6.0 to 7.5 for a thirty minute to two hour period. This allows the ingredients to be absorbed in his stomach, while preventing unpleasant reactions in his stomach. The base alkalizer composition can include the combination of a calcium carbonate carrier which acts as a mild alkalizer, an hydroxide (magnesium or potassium) which acts as a fast alkalizer, and a phosphate (dicalcium or tricalcium) which acts as a moderate alkalizer and which also maintains the pH fairly stable over a twenty to forty minute time period.

7 Claims, 12 Drawing Sheets

PKA BUFFERED VITAMIN C COMPOSITION AND METHOD

BACKGROUND OF THE INVENTION

Vitamin C is a common dietary supplement typically taken in the form of pills or capsules to supplement the human diet. Taken as a supplement from fifty milligrams to 5,000 milligrams daily, vitamin C can support improved health and can improve the immune system. It is an important nutrient to help neutralize free radicals and promote maximum intercellular communication. However, it has to be consumed or replenished regularly since it is not retained in the body.

Commercially available vitamin C taken orally in supplements causes discomfort to many users. This is because the vitamin C reacts with the hydrochloric acid (HCL) in the user's stomach thereby generating excessive stomach acids. Specifically, vitamin C is very acidic with a pH of 4.2; and people with acid problems (44% of the U.S. population has either acid reflux or occasional heartburn) cannot tolerate this pH level. Although there are a number of common buffering tablets containing carbonate and bicarbonates that can be consumed with vitamin C to relieve this gastrointestinal stress, none of them is formulated to aid GERD reduction and the absorption and retention of the vitamin C.

SUMMARY OF THE PREFERRED EMBODIMENTS

The inventive composition when orally ingested is not only gentle to the user's stomach, but can also help replace calcium that the vitamin C might remove from the user's body.

Specifically, disclosed herein is a pKa buffered vitamin C composition which includes a base alkalizer composition mixed with vitamin C (calcium ascorbate or ascorbic acid). The base alkalizer composition preferably can be approximately 24% to 40% by weight and the ascorbic acid or calcium ascorbate can be preferably approximately 76% to 60%. When this vitamin C composition is orally administered to an individual (in capsule or tablet form), it is expected that a rapid neutralization of stomach acid will advantageously occur followed by a sustained pH of about 6.0 to about 7.5 for an about thirty minute to two hour period. This allows the ingredients to be absorbed while preventing unpleasant reactions in the individual's stomach. The base alkalizer composition can preferably include the combination of a calcium carbonate carrier which acts as a mild alkalizer, a hydroxide (magnesium or potassium) which acts as a fast alkalizer, and a phosphate (dicalcium or tricalcium) which acts as a moderate alkalizer and which also maintains the pH fairly stable over an about twenty to forty minute time period.

According to one embodiment of the invention, the pKa buffered vitamin C composition comprises an alkalizing base composition which includes (or consists of or consists essentially of) calcium carbonate, magnesium hydroxide, DC ascorbic acid, a binder (gum acacia), potassium hydroxide and dicalcium phosphate; and a vitamin C source mixed with the alkalizing base composition.

According to another preferred embodiment of the invention, the pKa buffered vitamin C composition comprises an alkalizing base composition which includes (or consists of or consists essentially of) calcium carbonate, potassium hydroxide, a binder (gum acacia), potassium bicarbonate, dicalcium phosphate and tricalcium phosphate; and a vitamin C source mixed with the alkalizing base composition.

According to a further preferred embodiment of the invention, the pKa buffered vitamin C composition comprises an alkalizing base composition which includes (or consists of or consists essentially of) calcium carbonate, potassium hydroxide, potassium carbonate and dicalcium phosphate; and a vitamin C source mixed with the alkalizing base composition.

According to a still further preferred embodiment of the invention, the alkalizing composition of the vitamin C composition may comprise any one or a combination of the following: sodium hydroxide, magnesium hydroxide, tricalcium phosphate, a vitamin, such as ascorbic acid and/or vitamin $D_3$, and a binder such as gum acacia.

Even further, the present invention includes methods (and compositions) for buffering high acid nutraceuticals, specifically (but not limited to) vitamin C to be taken orally as dietary supplements.

Other objects and advantages of the present invention will become more apparent to those persons having ordinary skill in the art to which the present invention pertains from the foregoing description taken in conjunction with the accompanying drawing.

BRIEF DESCRIPTION OF THE DRAWINGS

The drawing figures are graphs showing measurements of buffering effectiveness of the present invention over time for each of the formulations discussed in the following section of this disclosure.

DETAILED DESCRIPTION OF PREFERRED EMBODIMENTS OF THE INVENTION

A pKa buffered vitamin C composition of the present invention is formed by mixing, such as in a ribbon blender, an alkalizing base composition (numerous formulations of which are disclosed in detail in this disclosure) and vitamin C. The vitamin C can be powder or compressible-granular calcium ascorbate or ascorbic acid. The base alkalizer composition can be approximately 24% to 40% (or approximately 24%) by weight and the ascorbic acid or calcium ascorbate approximately 60% to 76% (or approximately 76%) of the vitamin C composition. The vitamin C composition thereby formed is packaged, for example, in fifty or twenty-five kilogram packages. The packages are delivered to a tablet or capsule manufacturer who puts the composition into tablet or capsule form as would be known and in sizes as would also be known by those skilled in the art. For tablets, a minimum of 240 milligrams of base composition to 500 milligrams of vitamin C may be included. While a preferred embodiment is 500 milligrams of vitamin C, it can be buffered just as well pursuant to this invention at 200 milligrams of vitamin C. Further, smaller tablets of 80 milligrams of base to 200 milligrams of vitamin C are also within the scope of the invention.

The alkalizing compositions may be produced as a granulated, agglomerate compound by milling, blending and spray drying the ingredients in a Shugi agglomerating system. The Shugi agglomerating system is a commercially available system that has been designed to agglomerate minerals to USP and pharmaceutical standards. It is designed to properly mix and agglomerate various ingredients with different molecular weights into a uniform granule.

The ingredients of the alkalizing composition can be first milled to a fine powder. The fine powder is then heated to thirty degrees to thirty-nine degrees Centigrade and pressure sprayed into an environment having a relative humidity of from about 9.0% to about 15.0%. The fine powder is then sprayed with a solution of gum acacia to achieve a uniform granule that is free-flowing, non-dusting, and highly compressible. Gum acacia aids in providing uniform finished granules.

The resulting granulated alkalizing compositions can have a pH in the range of from about 5.0 to about 13.0, from about 6.5 to about 11.5, or from about 8.0 to about 10.0.

The following alkalizing base compositions are suitable for use in the formulations and methods disclosed herein:

| Formulation #1 | |
|---|---|
| Ingredients | % by weight |
| calcium carbonate | 79.08% |
| magnesium hydroxide | 7.77 |
| DC ascorbic acid | 5.00 |
| gum *acacia* | 4.76 |
| potassium hydroxide | 1.99 |
| dicalcium phosphate | 1.40 |

In one embodiment, the alkalizing composition comprises from about 50% to about 99%, from about 60% to about 90%, or from about 70% to about 85% by weight calcium carbonate; from about 0.01% to about 10%, from about 0.01% to about 8%, or from about 5% to about 8% by weight magnesium hydroxide; from about 0.01% to about 10%, from about 0.01% to about 8%, or from about 0.01% to about 6% by weight ascorbic acid; from about 0.01% to about 10%, from about 0.01% to about 8%, or from about 0.01% to about 6% by weight gum acacia; from about 0.01% to about 10%, from about 0.01% to about 8%, or from about 0.01% to about 6% by weight potassium hydroxide; and from about 0.01% to about 10%, from about 0.01% to about 8%, or from about 0.01% to about 6% by weight dicalcium phosphate.

| Formulation #2 | |
|---|---|
| Ingredients | % by weight |
| calcium carbonate | 84.00% |
| potassium hydroxide | 4.50 |
| gum *acacia* | 4.50 |
| potassium bicarbonate | 2.90 |
| dicalcium phosphate | 2.90 |
| tricalcium phosphate | 1.20 |

In another embodiment, the alkalizing composition comprises from about 50% to about 99%, from about 60% to about 90%, or from about 75% to about 90% by weight calcium carbonate; from about 0.01% to about 10%, from about 0.01% to about 8%, or from about 0.01% to about 6% by weight potassium hydroxide; from about 0.01% to about 10%, from about 0.01% to about 6%, or from about 0.01% to about 4% by weight dicalcium phosphate; from about 0.01% to about 10%, from about 0.01% to about 6%, or from about 0.01% to about 4% by weight tricalcium phosphate; and from about 0.01% to about 10%, from about 0.01% to about 6%, or from about 0.01% to about 4% by weight potassium bicarbonate; and from about 0.01% to about 10%, from 0.01% to about 8%, from 0.01% to about 6%, or from about 1.0% to about 5% by weight gum acacia.

| Formulation #3 | |
|---|---|
| Ingredients | % by weight |
| calcium carbonate | 88.08% |
| potassium hydroxide | 6.00 |
| potassium bicarbonate | 4.00 |
| dicalcium phosphate | 1.92 |

In yet another embodiment, the alkalizing composition comprises: from about 50% to about 99%, from about 60% to about 95%, or from about 70% to about 90% by weight calcium carbonate; from about 0.01% to about 10%, from about 2% to about 8%, or from about 4% to about 7% by weight potassium hydroxide; from about 0.01% to about 10%, from about 0.01% to about 8%, or from about 0.01% to about 6% by weight potassium bicarbonate; and from about 0.01% to about 5%, from about 0.01% to about 4%, or from about 0.01% to about 3% by weight dicalcium phosphate.

| Formulation #4 | |
|---|---|
| Ingredients | % by weight |
| calcium carbonate | 80.48% |
| magnesium hydroxide | 7.77 |
| DC ascorbic acid | 5.00 |
| gum *acacia* | 4.76 |
| potassium hydroxide | 1.99 |

In another embodiment, the alkalizing composition comprises from about 50% to about 99%, from about 60% to about 90%, or from about 70% to about 85% by weight calcium carbonate; from about 0.01% to about 10%, from about 0.01% to about 8%, or from about 5% to about 8% by weight magnesium hydroxide; from about 0.01% to about 10%, from about 0.01% to about 8%, or from about 0.01% to about 6% by weight ascorbic acid; from about 0.01% to about 10%, from about 0.01% to about 8%, or from about 0.01% to about 6% by weight gum acacia, and from about 0.01% to about 10%, from about 0.01% to about 8%, or from about 0.01% to about 6% by weight potassium hydroxide.

| Formulation #5 | |
|---|---|
| Ingredients | % by weight |
| calcium carbonate | 82.00% |
| sodium hydroxide | 7.50 |
| dicalcium phosphate | 2.00 |
| potassium hydroxide | 2.05 |
| potassium bicarbonate | 1.65 |
| gum *acacia* | 4.80 |

| Formulation #6 | |
|---|---|
| Ingredients | % by weight |
| calcium carbonate | 82.00% |
| sodium hydroxide | 7.50 |
| dicalcium phosphate | 2.00 |

-continued

| Formulation #6 | |
|---|---|
| Ingredients | % by weight |
| potassium hydroxide | 2.00 |
| potassium bicarbonate | 3.00 |
| gum *acacia* | 4.00 |

In a further embodiment, the alkalizing composition comprises from about 50% to about 99%, from about 60% to about 90%, or from about 70% to about 85% by weight calcium carbonate; from about 0.01% to about 10%, from about 2% to about 10%, or from about 5% to about 9% by weight sodium hydroxide; from about 0.01% to about 10%, from about 0.01% to about 8%, or from about 0.01% to about 4% by weight dicalcium phosphate; from about 0.01% to about 10%, from about 0.01% to about 8%, or from about 0.01% to about 4% by weight potassium hydroxide; from about 0.01% to about 10%, from about 0.01% to about 8%, or from about 0.01% to about 4% by weight potassium bicarbonate; from about 0.01% to about 10%, from about 0.1% to about 8%, or from about 0.01% to about 6% by weight gum acacia.

| Formulation #7 | |
|---|---|
| Ingredients | % by weight |
| calcium carbonate | 80.48% |
| magnesium hydroxide | 7.77 |
| DC ascorbic acid | 5.00 |
| gum *acacia* | 4.77 |
| potassium hydroxide | 1.98 |

In accordance with another embodiment, the alkalizing composition may comprise from about 50% to about 99%, from about 60% to about 95%, or from about 70% to about 90% by weight calcium carbonate; from about 0.01% to about 10%, from about 0.01% to about 8%, or from about 0.01% to about 4% by weight magnesium hydroxide; from about 0.01% to about 10%, from about 0.01% to about 8%, or from about 0.01% to about 6% by weight ascorbic acid; from about 0.01% to about 10%, from about 0.01% to about 8%, or from about 0.01% to about 6% by weight gum acacia; and from about 0.01% to about 10%, from about 0.01% to about 6%, or from about 0.01% to about 4% by weight potassium hydroxide.

| Formulation #8 | |
|---|---|
| Ingredients | % by weight |
| calcium carbonate | 80.48% |
| magnesium hydroxide | 7.77 |
| gum *acacia* | 4.77 |
| DC ascorbic acid | 3.00 |
| dicalcium phosphate | 2.00 |
| potassium hydroxide | 1.98 |

| Formulation #9 | |
|---|---|
| Ingredients | % by weight |
| calcium carbonate | 79.40% |
| magnesium hydroxide | 7.20 |
| DC ascorbic acid | 4.77 |
| gum *acacia* | 3.00 |
| dicalcium phosphate | 2.00 |
| potassium hydroxide | 1.98 |
| potassium bicarbonate | 1.65 |

In another embodiment, the alkalizing composition comprises from about 50% to about 99% by weight, from about 60% to about 95% by weight, or from about 70% to about 90% by weight calcium carbonate; from about 0.01% to about 10%, from about 0.01% to about 8%, or from about 5% to about 8% by weight magnesium hydroxide; from about 0.01% to about 10% by weight, from about 0.01% to about 8%, or from about 0.01% to about 6% by weight gum acacia; from about 0.01% to about 10%, from about 0.01% to about 8%, or from about 0.01% to about 5% by weight ascorbic acid; from about 0.01% to about 10%, from about 0.01% to about 6%, or from about 0.01% to about 4% by weight dicalcium phosphate; and from about 0.01% to about 10%, from about 0.01% to about 6%, or from about 0.01% to about 4% by weight potassium hydroxide.

| Formulation #10 | |
|---|---|
| Ingredients | % by weight |
| calcium carbonate | 82.50% |
| magnesium hydroxide | 7.00 |
| dicalcium phosphate | 2.00 |
| potassium hydroxide | 2.00 |
| potassium bicarbonate | 1.50 |
| gum *acacia* | 5.00 |

In yet a further embodiment, the alkalizing composition comprises from about 50% to about 99%, from about 60% to about 90%, or from about 70% to about 85% by weight calcium carbonate; from about 0.01% to about 10%, from about 0.01% to about 8%, or from about 5% to about 8% by weight magnesium hydroxide; from about 0.01% to about 10%, from about 0.01% to about 8%, or from about 0.01% to about 5% by weight dicalcium phosphate; from about 0.01% to about 10%, from about 0.01% to about 6%, or from about 0.01% to about 4% by weight potassium hydroxide; from about 0.01% to about 10%, from about 0.01% to about 6%, or from about 0.01% to about 4% by weight potassium bicarbonate; from about 0.01% to about 10%, from about 0.01% to about 8%, or from about 0.01% to about 6% by weight gum acacia. The alkalizing composition may further comprise a vitamin, such as ascorbic acid.

In another embodiment, the alkalizing composition can comprise calcium carbonate, magnesium hydroxide, DC ascorbic acid, gum acacia, potassium hydroxide, and dicalcium phosphate. Optionally, the alkalizing composition can contain vitamin D3.

The following additional formulations may be used to produce suitable alkalizing compositions for use in connection with the methods and vitamin C compositions disclosed herein:

| Formulation #11 | |
|---|---|
| Ingredients | % by weight |
| calcium carbonate | 80.48% |
| magnesium hydroxide | 7.77 |
| DC ascorbic acid | 5.00 |
| gum *acacia* | 4.76 |
| potassium hydroxide | 1.99 |

| Formulation #12 | |
|---|---|
| Ingredients | % by weight |
| calcium carbonate | 79.08% |
| magnesium hydroxide | 7.77 |
| DC ascorbic acid | 5.00 |
| gum *acacia* | 4.76 |
| potassium hydroxide | 1.99 |
| dicalcium phosphate | 1.40 |

In one embodiment, the alkalizing composition can comprise calcium carbonate, magnesium hydroxide, DC ascorbic acid, gum acacia, potassium hydroxide, and optionally vitamin D3.

Figure 1:
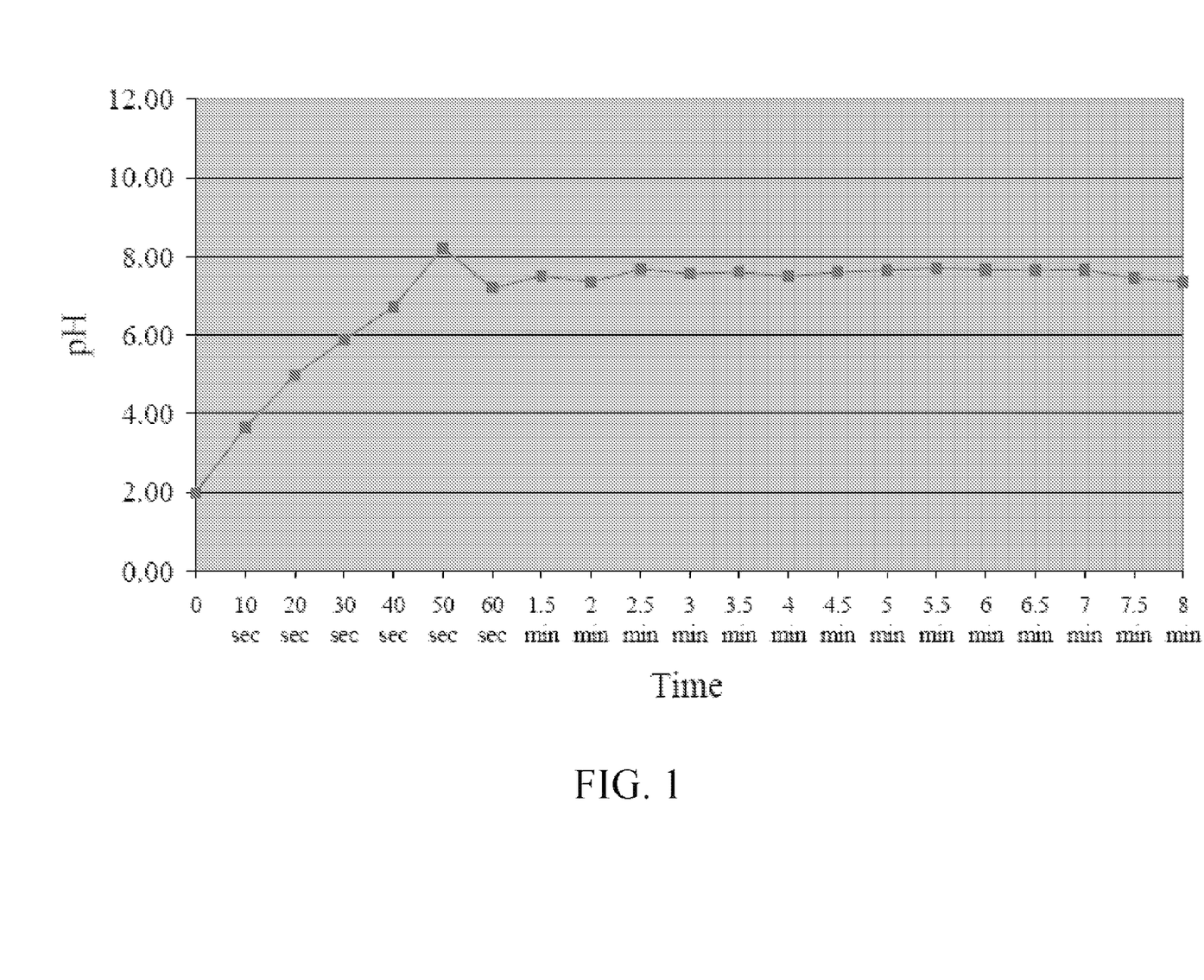
FIG. 1 shows the test results for formulation #1.
Figure 2:
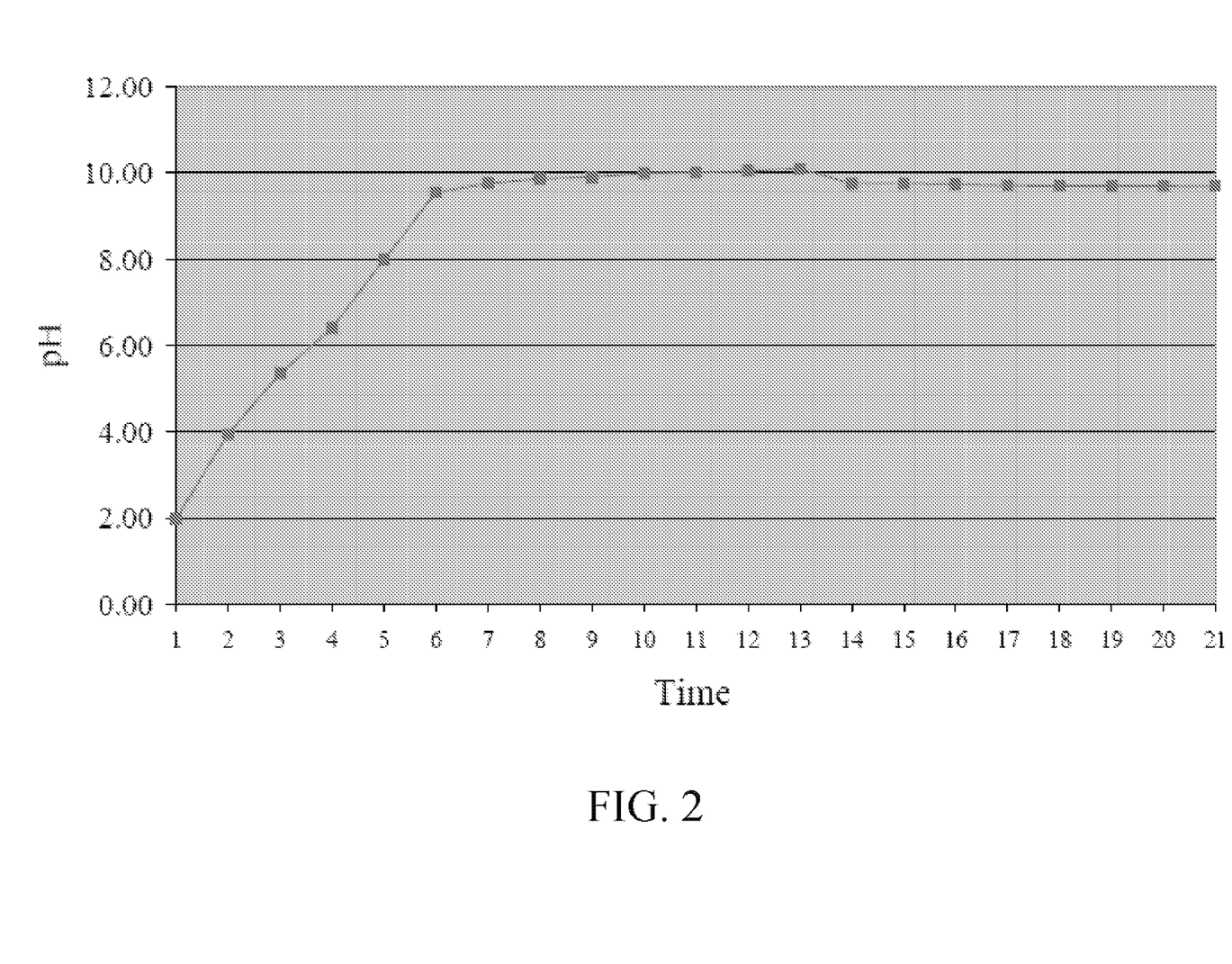
FIG. 2 shows the test results for formulation #2.
Figure 3:
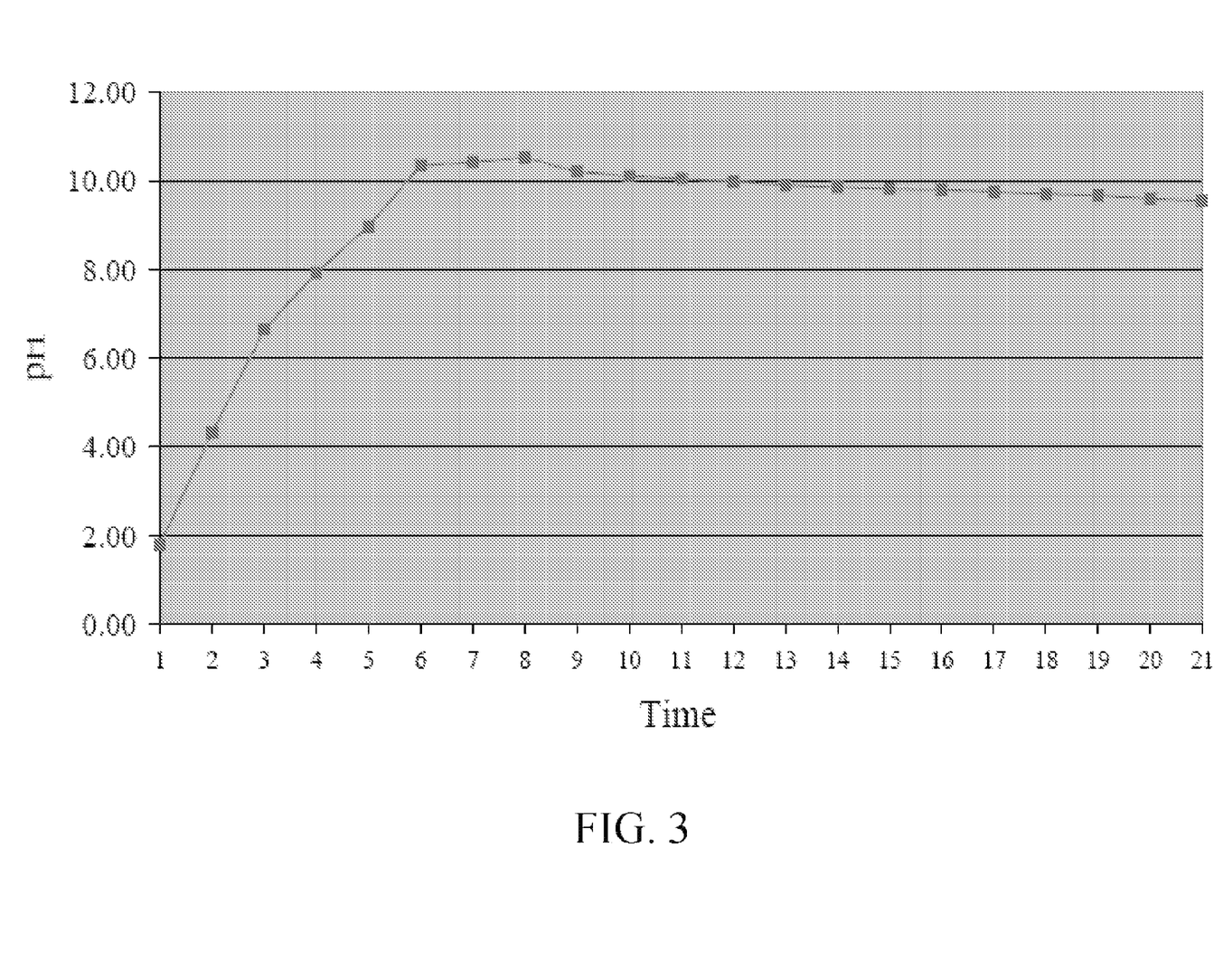
FIG. 3 shows the test results for formulation #3.
Figure 4:
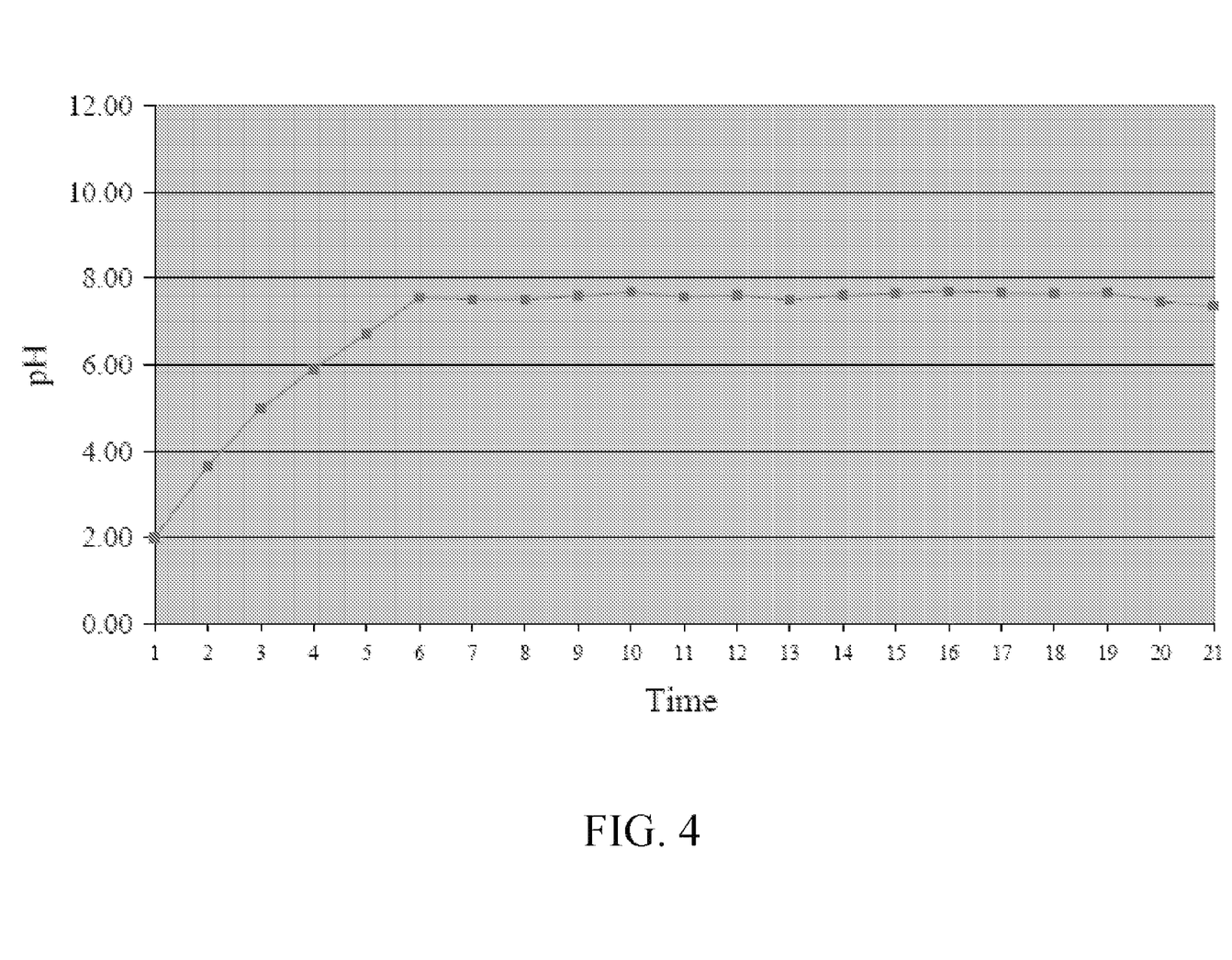
FIG. 4 shows the test results for formulation #4.
Figure 5:
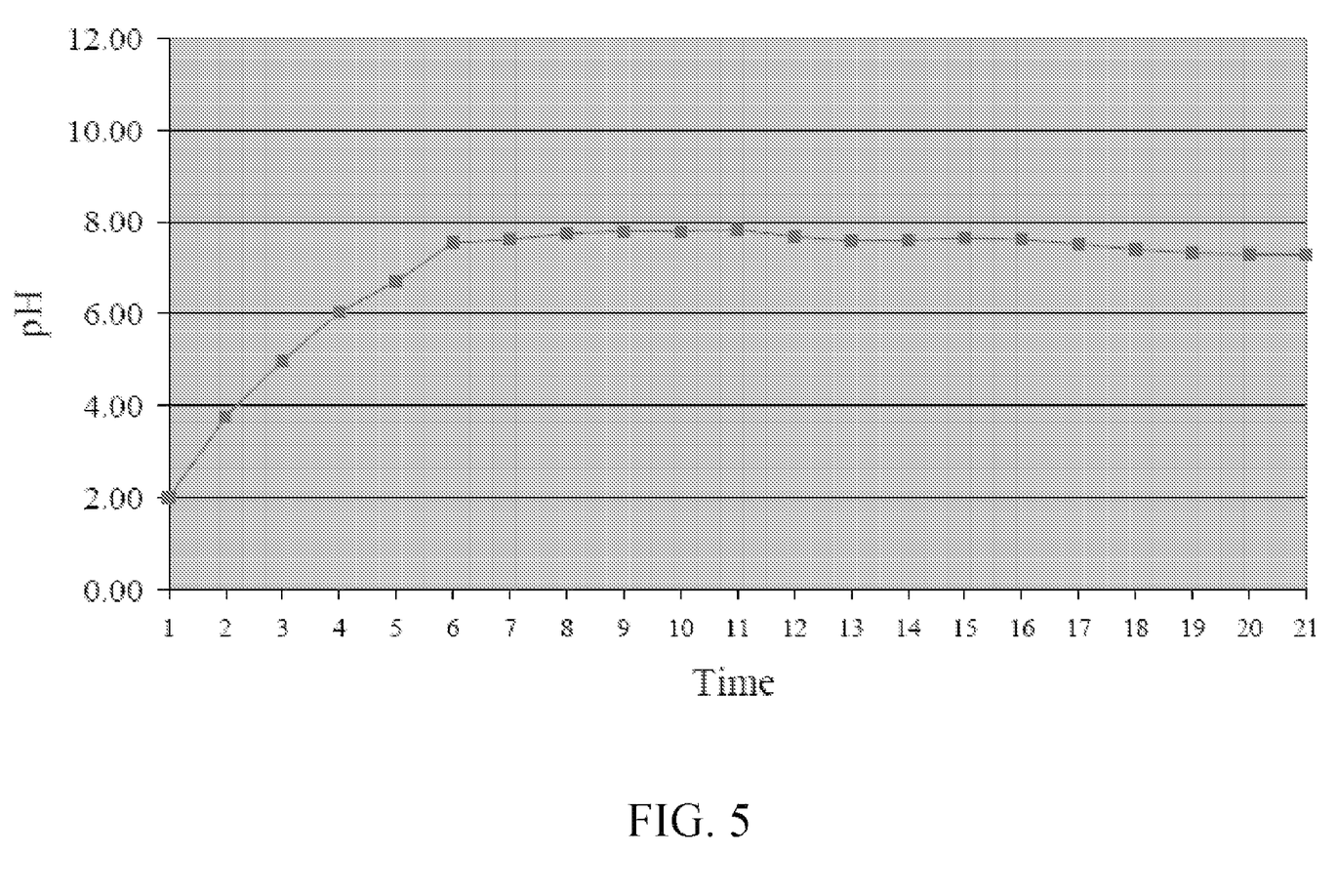
FIG. 5 shows the test results for formulation #5.
Figure 6:
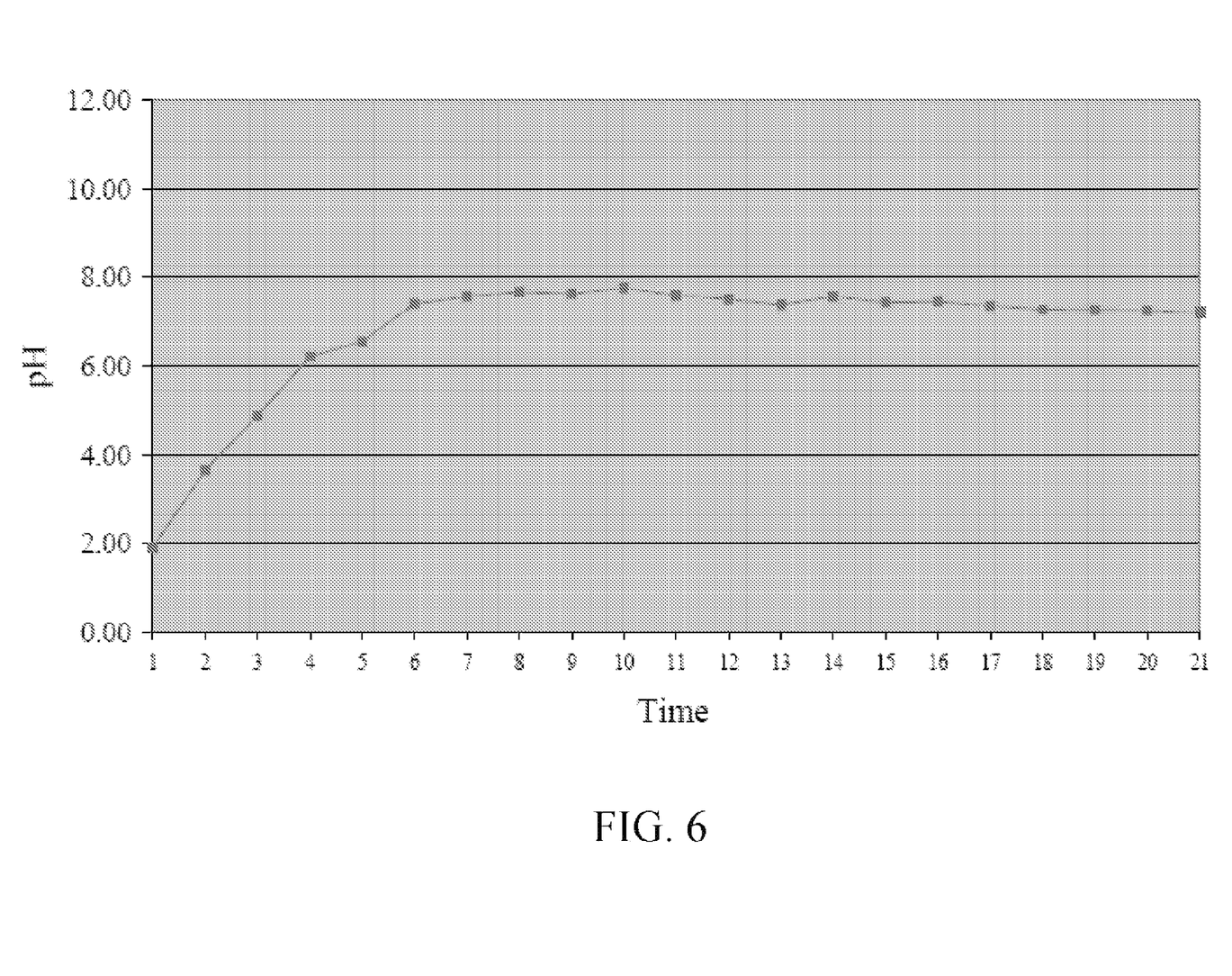
FIG. 6 shows the test results for formulation #6.
Figure 7:
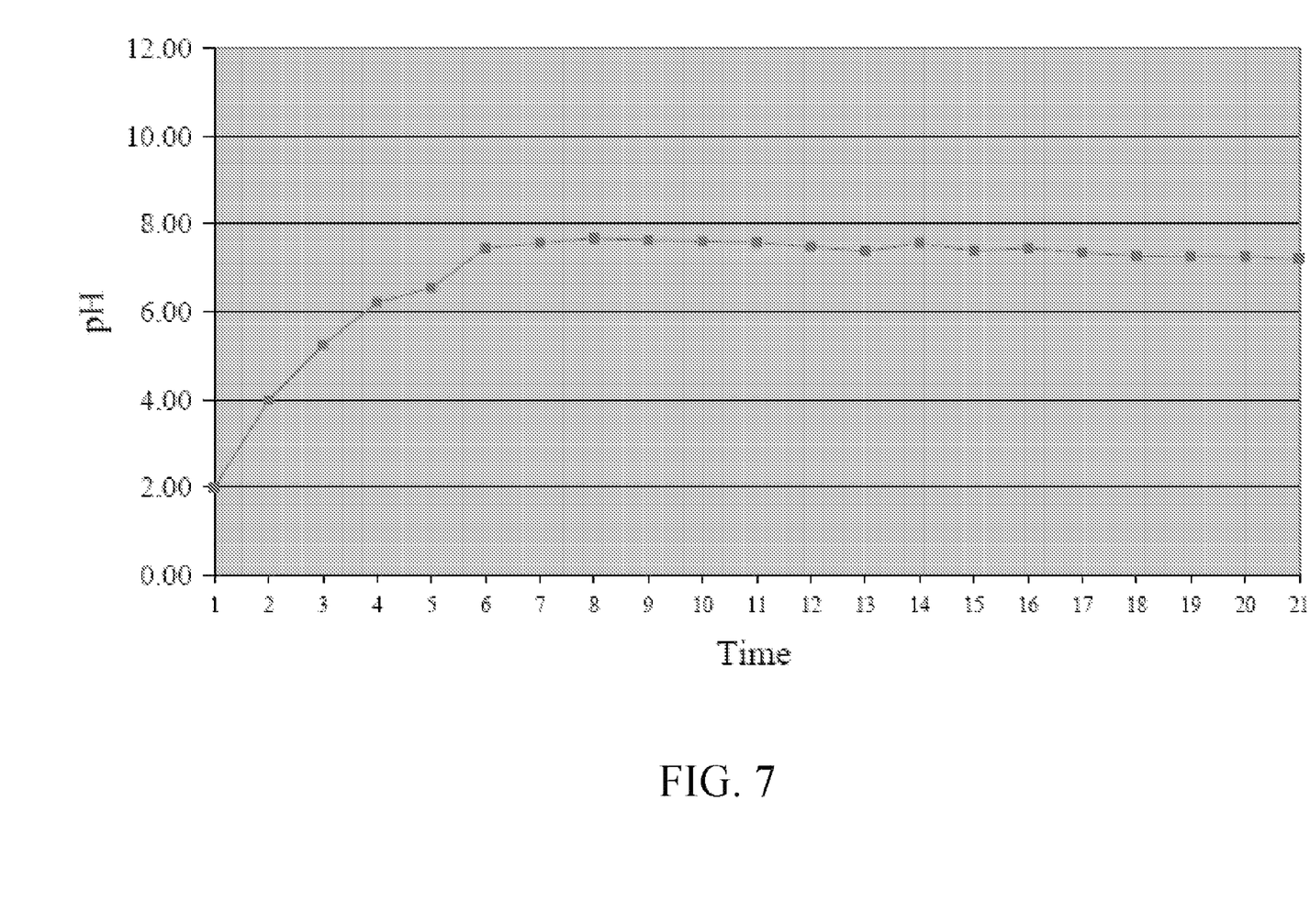
FIG. 7 shows the test results for formulation #7.
Figure 8:
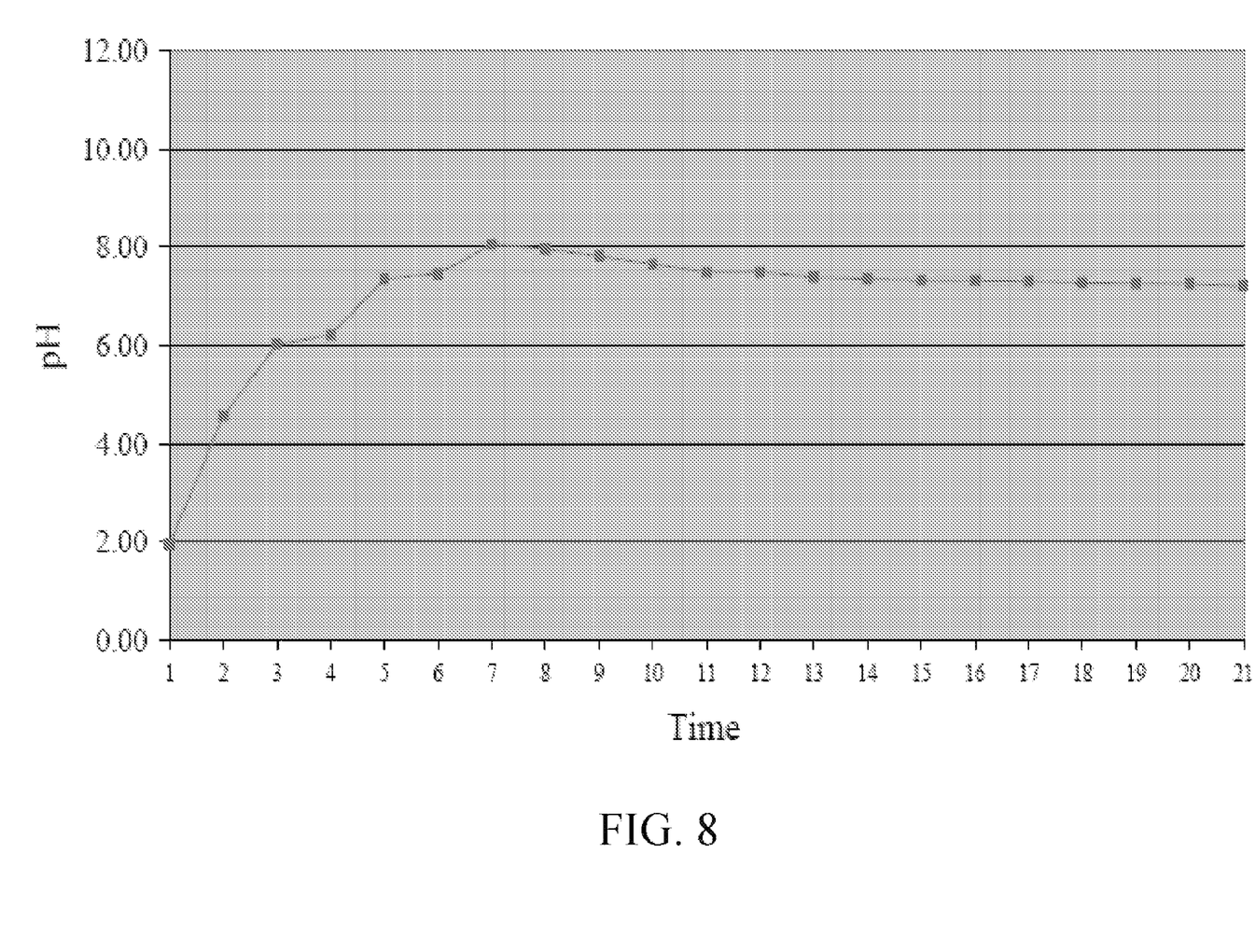
FIG. 8 shows the test results for formulation #8.
Figure 9:
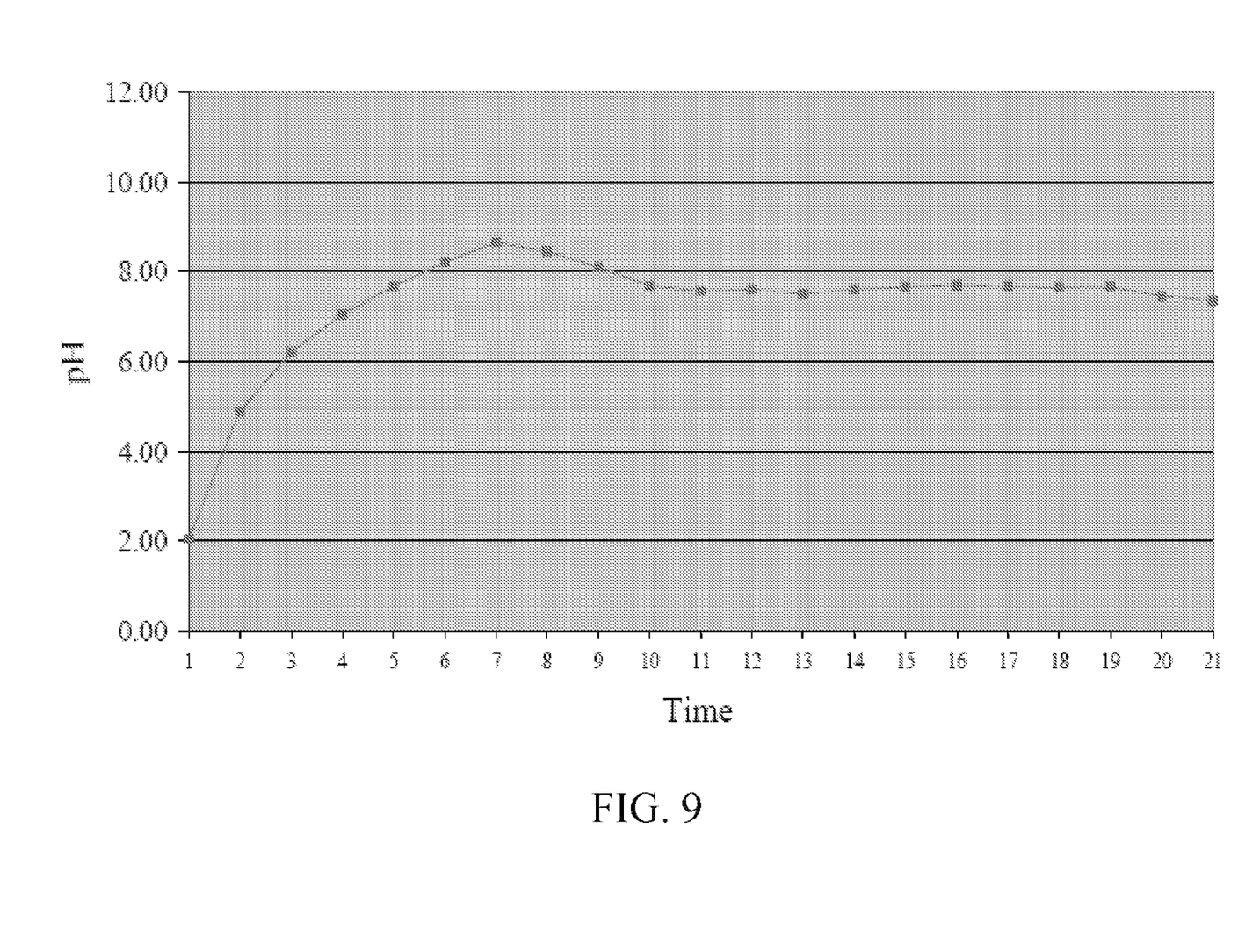
FIG. 9 shows the test results for formulation #9.
Figure 10:
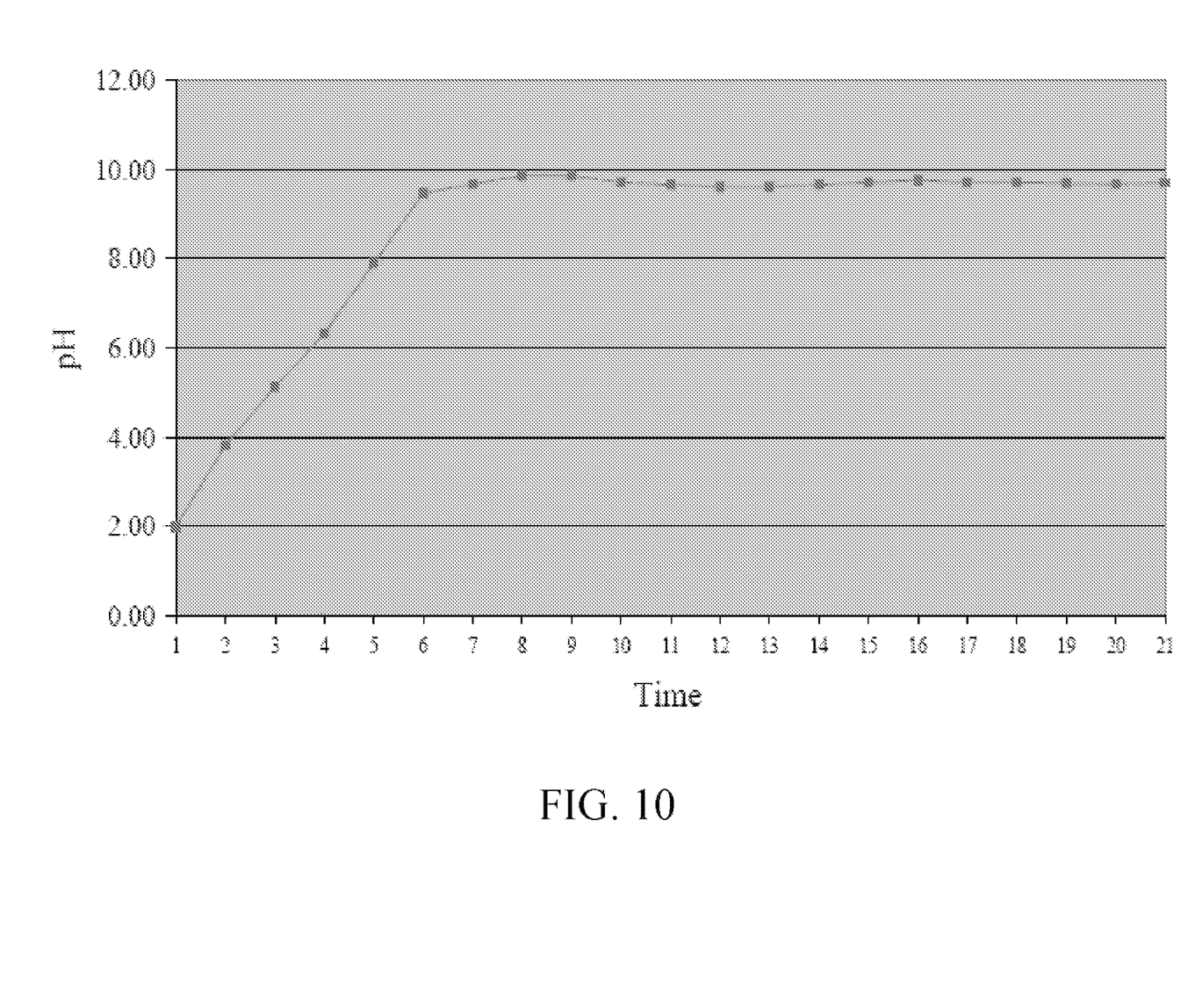
FIG. 10 shows the test results for formulation #10.
Figure 11:
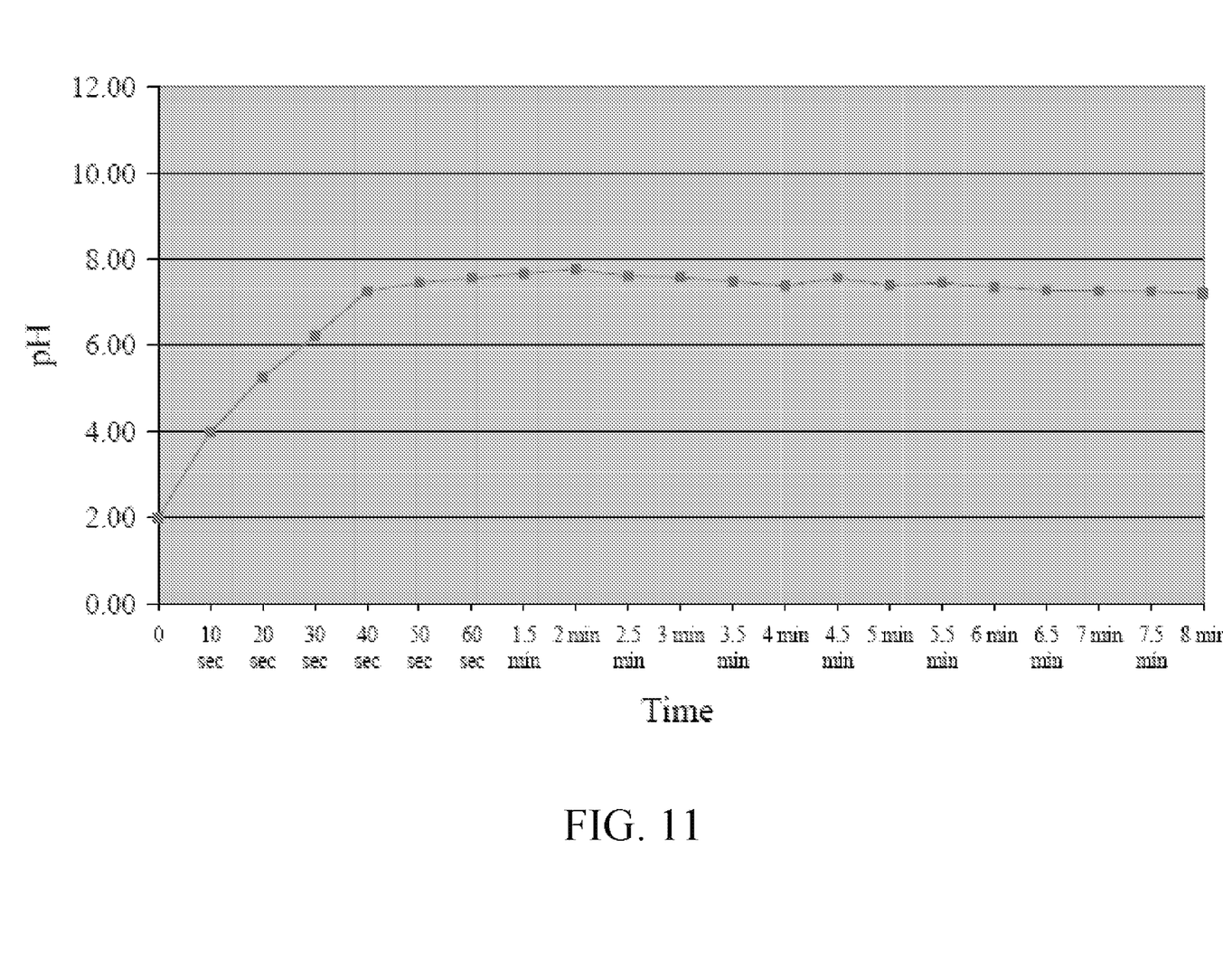
FIG. 11 shows the test results for formulation #11.
Figure 12:
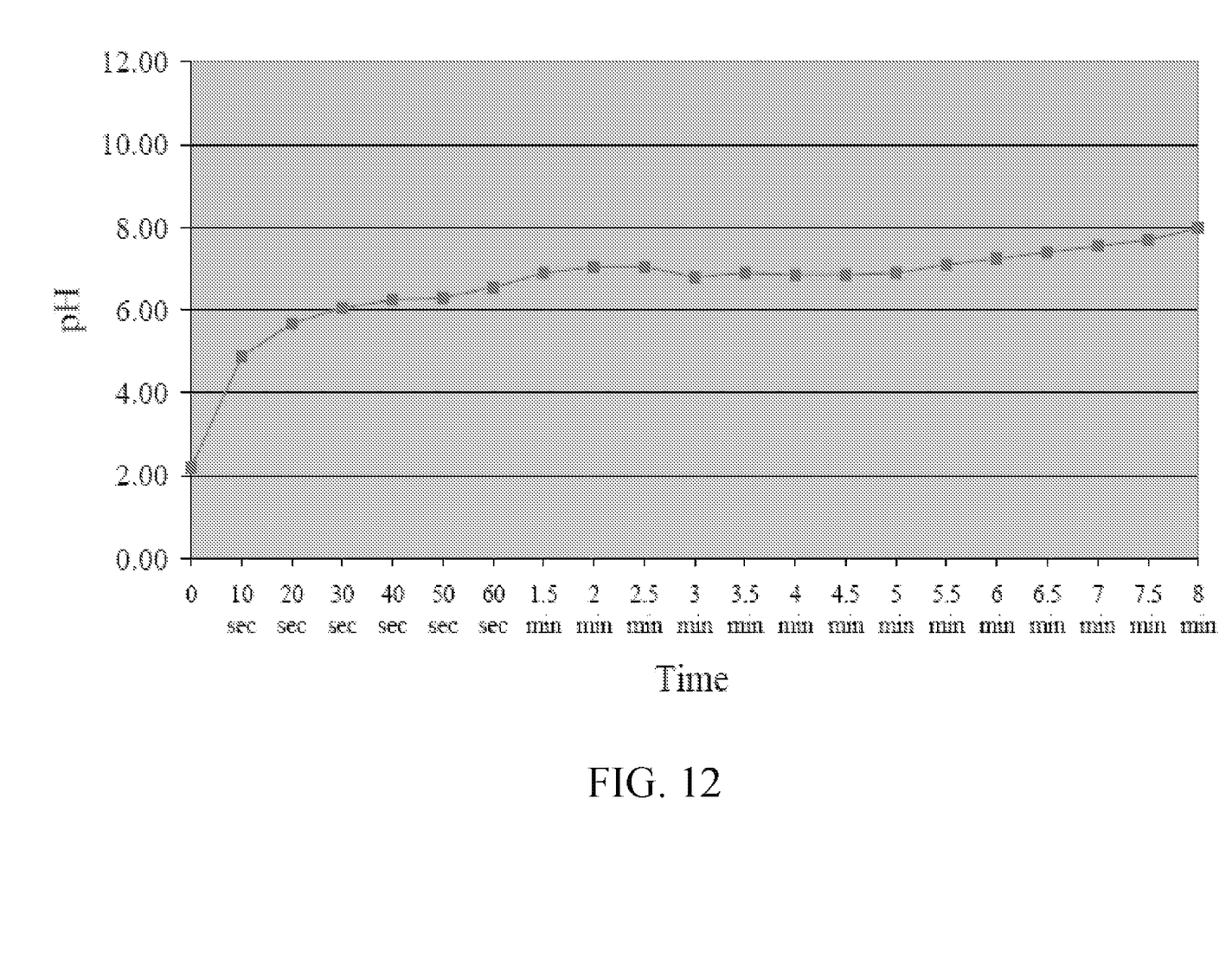
FIG. 12 shows the test results for formulation #12.

Anticipated functioning of calcium ascorbate and each of formulations #1-#12, as discussed above, of the present invention in the user's stomach are illustrated in the chart of the drawing figures. Each of the charts of the drawing figures shows test results for the neutralization of 100 grams solution of 0.015 M hydrochloric acid (HCL) (pH 2.00) by 300 milligrams of a respective formulation sample.

Referring to the drawing figures, the present invention, due to its high pKa, immediately neutralizes the stomach acid to a pH of 7.0 in one minute and a pH of 7.5 after eight minutes. Some people receive an added benefit because the temporary chelating of calcium supplied by the invention temporarily protects vitamin C (ascorbate ion) from oxidation to dehyroascorbic acid and subsequent rapid oxidative degradation in the duodenum. Additionally, some individuals absorb only a few milligrams of vitamin C (ascorbate) out of each gram of ascorbic acid ingested, and thus they will benefit from vitamin C chelated as calcium, magnesium or potassium ascorbate.

From the foregoing detailed description, it will be evident that there are a number of changes, adaptations and modifications of the present invention which come within the province of those skilled in the art. For example, the present invention includes all of the formulations disclosed herein. Further, the scope of the invention includes any combination of the elements from the different species, formulations or embodiments disclosed herein, as well as subassemblies, assemblies, and methods of using and making thereof, and combinations of the various percentage ranges. It is intended that all such variations not departing from the spirit of the invention be considered as within the scope thereof.

What is claimed is:

1. An alkalizing base composition consisting of from about 50 to about 99% by weight of calcium carbonate; from about 0.01 to about 10% by weight of magnesium hydroxide; from about 0.01 to about 6% by weight of ascorbic acid; from about 0.01 to about 10% by weight gum acacia; and from about 0.01% to about 10% by weight potassium hydroxide.

2. An alkalizing base composition consisting of from about 50 to about 99% by weight of calcium carbonate; from about 0.01 to about 10% by weight of magnesium hydroxide; from about 0.01 to about 6% by weight of ascorbic acid; from about 0.01 to about 10% by weight gum acacia; from about 0.01% to about 10% by weight potassium hydroxide; and from about 0.01% to about 10% by weight of dicalcium phosphate.

3. An alkalizing base composition consisting of from about 50 to about 99% by weight of calcium carbonate; from about 0.01 to about 10% by weight of magnesium hydroxide; from about 0.01 to about 6% by weight of ascorbic acid; from about 0.01 to about 10% by weight gum acacia; from about 0.01% to about 10% by weight potassium hydroxide; and from about 0.01 to about 10% by weight potassium bicarbonate.

4. An alkalizing base composition consisting of from about 50 to about 99% by weight calcium carbonate; from about 0.01 to about 10% by weight potassium hydroxide; from about 0.01 to about 10% by weight potassium bicarbonate; and from about 0.01 to about 3% by weight dicalcium phosphate.

5. An alkalizing base composition consisting of from about 50 to about 99% by weight of calcium carbonate; from about 0.01 to about 10% by weight potassium hydroxide; from about 0.01 to about 10% by weight potassium bicarbonate; from about 0.01 to about 3% by weight dicalcium phosphate; and from about 0.01 to about 10% by weight tricalcium phosphate and from about 1.0 to about 5% by weight gum acacia.

6. An alkalizing base composition consisting of from about 50 to about 99% by weight calcium carbonate; from about 0.01 to about 10% by weight sodium hydroxide; from about 0.01 to about 10% by weight dicalcium phosphate; from about 0.01 to about 10% by weight potassium hydroxide; from about 0.01 to about 10% by weight potassium bicarbonate; and from about 0.01 to about 10% by weight gum acacia.

7. An alkalizing base composition consisting of from about 50 to 99% by weight calcium carbonate; from about 0.01 to about 10% by weight magnesium hydroxide; from about 0.01 to about 10% by weight dicalcium phosphate; from about 0.01 to about 10% by weight potassium hydroxide; and from about 0.01 to about 10% by weight potassium bicarbonate; and from about 0.01 to about 10% by weight gum acacia.

* * * * *